United States Patent [19]

Zee et al.

[11] Patent Number: 4,632,980

[45] Date of Patent: Dec. 30, 1986

[54] OZONE DECONTAMINATION OF BLOOD AND BLOOD PRODUCTS

[75] Inventors: Yuan C. Zee, Davis, Calif.; David C. Bolton, Staten Island, N.Y.

[73] Assignee: Immunologics, San Francisco, Calif.

[21] Appl. No.: 719,187

[22] Filed: Apr. 3, 1985

[51] Int. Cl.[4] ..................... A61K 35/14; A61K 35/16; C07K 3/08; C07K 3/12
[52] U.S. Cl. ..................... 530/380; 424/101; 514/2; 514/8; 514/21; 530/351; 530/363; 530/381; 530/382; 530/383; 530/384; 530/385; 530/387; 530/829; 530/830
[58] Field of Search ............ 260/112 B; 424/101; 530/351, 380, 381, 382, 383, 384, 385, 387, 363, 830, 829; 514/2, 8, 21

[56] References Cited

U.S. PATENT DOCUMENTS

| 4,183,962 | 1/1980 | Asher | 424/101 X |
| 4,540,573 | 9/1985 | Neurath et al. | 424/101 X |
| 4,581,231 | 4/1986 | Purcell et al. | 424/101 |

FOREIGN PATENT DOCUMENTS

0086071  8/1983  European Pat. Off.

OTHER PUBLICATIONS

Chem. Abstracts, vol. 102, 1985, 126730f, Ignatenko et al.

*Primary Examiner*—Howard E. Schain
*Attorney, Agent, or Firm*—Bertram I. Rowland

[57] ABSTRACT

Blood and proteinaceous blood products employed for their physiological and/or immunological properties are free of viable enveloped viruses by treatment with low levels of ozone, levels at which substantially all of the physiological and/or immunological activity is retained.

6 Claims, No Drawings

OZONE DECONTAMINATION OF BLOOD AND BLOOD PRODUCTS

BACKGROUND OF THE INVENTION

1. Field of the Invention

Human blood finds a wide variety of applications and uses, being used not only in transfusions, but also as a source for individual proteinaceous components. For many diseases, the human host is defective in producing an essential factor, such as one of the factors involved in the clotting cascade, where whole blood is used as a source for such protein. The increasing needs for blood has encouraged the employment of both domestic and foreign sources. In the case of whole blood, usually a pint is from a single individual, so that any contamination, as bad as it may be, will be limited to a single individual. By contrast, where components are isolated and used, frequently the blood will be pooled from a large number of different donors. Thus, the presence of contamination from a single donor can compromise the use of the entire batch.

There appears to be an increasing awareness of the incidence of viral diseases associated with blood. Of recent date is the concern with the lymphadenopathy virus or human T-cell lymphotropic virus-III (LAV/HTLV-III). While there is an increasing effort to screen blood for the presence of the AIDS viral agent as well as other viruses, such as hepatitis virus, there is still the possibility for a significant number of false negatives which could result in the transfer of the infectious agent, particularly to an immunocompromised host. There is, therefore, substantial interest in finding ways to ensure that none of the blood or blood components which are to be administered to a human host have any viable infectious agent.

2. Brief Description of the Prior Art

European Patent Application No. 0 086 071 describes the use of ozone to inactivate enveloped viruses for use as a vaccine.

SUMMARY OF THE INVENTION

Blood and proteinaceous blood components are freed of infectious enveloped viral agents by treating the blood under mild conditions for a short period of time, where any virus is inactivated, while retaining the physiological properties of the blood or blood components.

DESCRIPTION OF THE SPECIFIC EMBODIMENTS

In accordance with the subject invention, methods and compositions are provided involving the freeing of blood or blood components of infectious enveloped viruses, while retaining the physiological properties of the blood or blood component, to provide compositions which may be introduced into a mammalian host without transmission of such viral infection.

In freeing or decontaminating the blood or blood-derived biological composition, an aqueous medium will be employed, which aqueous medium includes the blood without modification or a blood product which is less than whole blood, e.g, serum, clotting factors, or the like. The blood component will be treated in an aqueous medium. The aqueous medium is contacted with an enveloped virus deactivating amount of ozone for a short time under mild conditions and the aqueous medium removed from the ozone treatment, and may be subject to further treatment such as contact with a reducing agent. The resulting composition is freed of viable enveloped virus and may be used for administration to a mammalian host, normally a human host.

The biological compositions which are employed in this invention will be aqueous protein compositions involving blood or blood components. Whole blood, packed red cells, platelets, and plasma (fresh or fresh frozen) are exemplary. Other blood components of interest include plasma protein portion, anti-hemophilic factor (Factor VIII); Factor IX, and Factor IX complex (Factors II, VII, IX and X); fibrinogens, Factor XIII, prothrombin and thrombin (Factors II and IIa); immunoglobulins (IgA, -D, -E, -G, and -M); hyper-immune globulins; cryoprecipitate; albumin; interferons; lymphokines; transfer factor; etc.

In other than blood, the protein compositions in the aqueous media will generally range from about 1 μg/ml to about 500 mg/ml, usually from about 1-100 mg/ml. The pH will normally be close to the physiologic pH 7.4, usually being in the range of about 6-9, more usually about 7-8. Other components which may be present in the medium, include salts, additives, buffers, stabilizers or the like. These components will be conventional to the use of the particular blood product.

The subject method is effective with a wide variety of enveloped viruses, both RNA and DNA. Illustrative viruses include hepatitis virus, HTLV-I, -II, and -III, influenza virus, etc.

In decontaminating the blood or blood product, the medium may be contacted with the ozone under a variety of conditions. Generally, a bubbling of the ozone through the blood will not be employed, particularly where red blood cells are present, since this may lead to hemolysis. Various techniques for contacting the medium with the ozone may include pumping the medium through a chamber containing the ozone, employing a thin film, either by using a falling film or by using rotating vessels, e.g., rotating bottles, by passing the blood through porous fibers, such as hollow fibers, where the chamber containing the fibers contains the ozone, or by using tubing such as Gore-Tex®, P T F E tubing, where the medium is in contact with an ozone atmosphere. The concentration of ozone in the atmosphere will generally be from about 1–100 ppm, usually from about 1–20 ppm, remaining gases may be inert gases, such as nitrogen, or may be air. The temperature may be maintained from about 4°–37° C., more usually from about 4°–30° C., and preferably from about 4° to room temperature. The time will vary widely, depending upon the nature of the suspected contamination, generally employing about 0.5 hr and not more than about 4 days, more usually from about 0.5 hr to about 1 day.

After the medium containing the blood or blood component has been treated, it may be further treated with reducing agents to ensure the absence of any active oxygen. Small amounts of ascorbic acid, glutathione, sodium thionite, or the like, namely reducing agents which are physiologically acceptable, may be employed. The amounts will generally range from about 20 μg to about 2 mg/ml.

After the blood or blood components has been decontaminated, it may then be isolated and used directly for its intended purpose.

The following examples are offered by way of illustration and not by way of limitation.

EXPERIMENTAL

Ozone exposure system:

The system accommodates two vessels for ozone exposure. To prevent the reaction of ozone with non-biological components of the system, all the system components which come into contact with ozone are made with the inert materials glass, Teflon ® or stainless steel. Compressed air (3.5 kg/cm$^2$) is introduced into the system through a pressure regulator set at 141 g/cm$^2$ and is filtered through two ultrafilters (Mine Safety Appliances Co., Pittsburgh, PA) in series. Each ultrafilter is rated at 99.99% efficiency for particles of 0.3 μm diameter and contains a supplemental charcoal element.

Ozone at approximately 2 ppm is introduced into the system and mixed with the filtered air using two regulating valves to adjust the ozone concentrations. The main flow of the gas is directed into a room temperature incubator which houses the humidifying bubblers, the roller apparatus and the sequential sampler. The flow rate of gas through each exposure vessel is held constant by diverting around the sequential sampler a flow rate of gas equal to that sampled. The biological material to be exposed is in sterile 11 cm×29 cm borosilicate glass roller bottles (New Brunswick Scientific, New Brunswick, N.J.) equipped with specially machined roller caps with Viton seals. The bottles are rotated at a rate of 1.5 rpm during exposure to permit the ozone to react with the samples with only a thin film of fluid over most of the bottle surface.

Ozone generation and monitoring:

Ozone is generated in medical grade oxygen by silent electric arc discharge with a Sander Model IV Ozoniser (Erwin Sander Elektroapparatebau G.m.b.H. and Co., Am Osterberg, W. Germany) regulated by a constant voltage power supply.

Exposure of blood to ozone:

Whole blood is used containing 10$^9$ pfu/ml of hepatitis virus. 250 ml aliquots of the contaminated blood to be exposed is placed in two 11 cm×29 cm borosilicate glass roller culture bottles equipped with specially designed caps. The bottles are connected to the exposure system and rotated at 1.5 rpm at 20° C. while the humidified gas (2 ppm ozone) is flowed through the bottles at a rate of 6 L/min. The blood is exposed for 48 hr.

The ozone-treated blood is then tested for the presence of viable virus by inoculating susceptible chimpanzees.

The subject invention provides for a rapid, reliable, economic procedure for decontaminating blood and blood products, freeing the products of enveloped viruses, so that the products may be used without transmission of viral infection. Furthermore, the blood and blood products retain their physiological character, with minimal lysis of red blood cells and substantially complete maintenance of physiological activity of the protein components. The method is easy to perform, large amounts of blood can be treated, and the system is free of production of products which may have deleterious biological effects.

Although the foregoing invention has been described in some detail by way of illustration and example for purposes of clarity of understanding, it will be obvious that certain changes and modifications may be practiced within the scope of the appended claims.

What is claimed is:

1. A method for freeing blood and blood components of viable enveloped viruses while retaining the physiological characteristics of the blood or blood component, said method comprising:

contacting said blood or blood product in an aqueous medium with an enveloped virus inactivating amount of ozone under mild conditions for a sufficient time to inactivate all enveloped viruses present; and isolating the blood or blood component free of viable enveloped viruses.

2. A method according to claim 1, wherein said contacting is at a temperature in the range of 4° to 37° C. and at an ozone concentration of 1 to 100 ppm.

3. A method according to claim 2, wherein said blood or blood component is contacted as a thin film.

4. A method according to claim 2, wherein the contacting is for a duration of 0.5 hr to 4 days.

5. A method according to claim 2, wherein blood is contacted with ozone.

6. A method according to claim 2, wherein an aqueous solution of a blood component is contacted with ozone.

* * * * *

REEXAMINATION CERTIFICATE (1313th)

United States Patent [19]

Zee et al.

[11] B1 4,632,980

[45] Certificate Issued Jun. 26, 1990

[54] OZONE DECONTAMINATION OF BLOOD AND BLOOD PRODUCTS

[75] Inventors: Yuan C. Zee, Davis, Calif.; David C. Bolton, Staten Island, N.Y.

[73] Assignee: Medizone International, Inc., New York, N.Y.

Reexamination Request:
No. 90/001,799, Jun. 23, 1989

Reexamination Certificate for:
Patent No.: 4,632,980
Issued: Dec. 30, 1986
Appl. No.: 719,187
Filed: Apr. 3, 1985

[51] Int. Cl.$^5$ .................... A61K 35/14; A61K 35/16; C07K 3/08; C07K 3/12
[52] U.S. Cl. .................................. 530/380; 424/101; 514/2; 514/8; 514/21; 530/351; 530/363; 530/381; 530/382; 530/383; 530/384; 530/385; 530/387; 530/829; 530/830
[58] Field of Search ............... 530/351, 363, 380, 381, 530/382, 383, 384, 385, 387, 829, 830; 514/2, 8, 4

[56] References Cited

U.S. PATENT DOCUMENTS 2,637,688  5/1953  Ryan .
3,063,904  11/1962  Ryan .
3,715,430  2/1973  Ryan .
4,632,980  12/1986  Zee .................................. 530/380

OTHER PUBLICATIONS

Environmental Research, 43, 410–416 (1987), Meadows et al.
Ozone v. Hepatitis & Herpes-The Choice, Heinz Konrad, M.D.
The Treatment of Viral Hepatitis with Ozone-Oxygen Gas Mixture, Harmut Dorestewitz, M.D.
Ozone as a Therapy in Herpes Simplex & Herpes Zoster Diseases, Matassi, M.D., D'Angelo, M.D., Franchina, M.D., Bassi, M.D.
Medical Applications of Ozone, Julius LaRaus (editor).
Protides of the Biological Fluids Proceedings of the Colloquium, vol. 29, Pergamon Press, 129-132 (1982) Verweig et al.
Soc. Exp. Biol. Med. Proc., 126, 356-358 (1967), Goldstein et al.
Biophysics, vol. 30, No. 1, pp. 14–19 (1985), Ignatenko et al.
Atmospheric Environment, vol. 3, pp. 669-682 (1969), Mudd et al.

*Primary Examiner*—Howard E. Schain

[57] ABSTRACT

Blood and proteinaceous blood products employed for their physiological and/or immunological properties are free of viable enveloped viruses by treatment with low levels of ozone, levels at which substantially all of the physiological and/or immunological activity is retained.

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1-6 is confirmed.

* * * * *